United States Patent [19]
Siposs

[11] Patent Number: 4,758,224
[45] Date of Patent: * Jul. 19, 1988

[54] SUCTION CONTROL VALVE FOR LEFT VENTRICLE VENTING

[76] Inventor: George G. Siposs, 2855 Velasco La., Costa Mesa, Calif. 92626

[*] Notice: The portion of the term of this patent subsequent to Feb. 10, 2004 has been disclaimed.

[21] Appl. No.: 53,844

[22] Filed: May 26, 1987

Related U.S. Application Data

[63] Continuation-in-part of Ser. No. 884,190, Jul. 10, 1986, Pat. No. 4,725,266, which is a continuation-in-part of Ser. No. 715,928, Mar. 25, 1985, Pat. No. 4,642,097.

[51] Int. Cl.$^4$ ............................................. F16K 17/164
[52] U.S. Cl. ..................... 604/119; 604/118; 604/129; 604/247; 137/512.3
[58] Field of Search ................ 604/34, 35, 118, 119, 604/128, 129, 236, 237, 247; 137/512.3, 853

[56] References Cited

U.S. PATENT DOCUMENTS

| | | | |
|---|---|---|---|
| 3,384,113 | 5/1968 | Pennisi | 137/853 |
| 3,995,617 | 12/1976 | Watkins et al. | 604/247 |
| 4,502,502 | 3/1985 | Krug | 604/118 |
| 4,642,097 | 2/1987 | Siposs | 604/118 |
| 4,657,536 | 4/1987 | Dorman | 604/247 |
| 4,671,786 | 6/1987 | Krug | 604/118 |
| 4,725,266 | 2/1988 | Siposs | 604/119 |

Primary Examiner—Stephen C. Pellegrino
Assistant Examiner—Ralph Lewis

[57] ABSTRACT

The valve is positioned in the left ventricle drain line and includes a check valve which permits flow only away from the heart. A vent valve is located downstream of the check valve to prevent buildup of pressure. In addition, the valve includes an inwardly directed umbrella valve to limit left ventricle drain line vacuum intensity applied to the heart.

12 Claims, 1 Drawing Sheet

U.S. Patent  Jul. 19, 1988  4,758,224
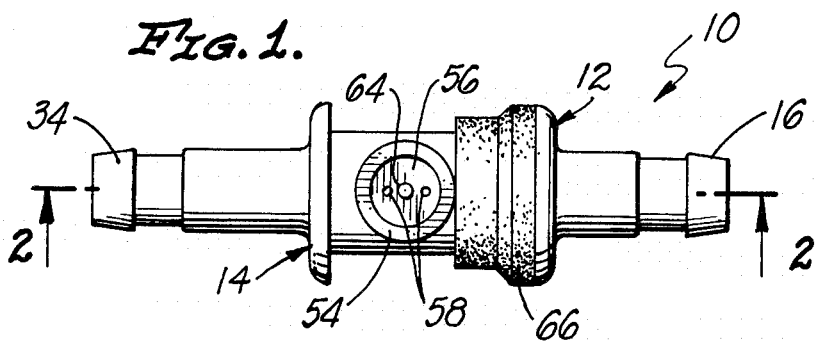
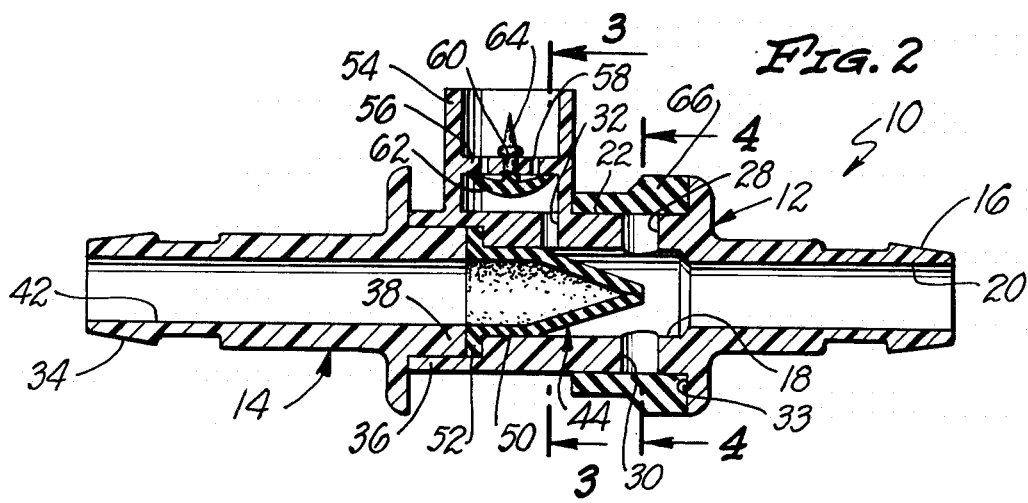
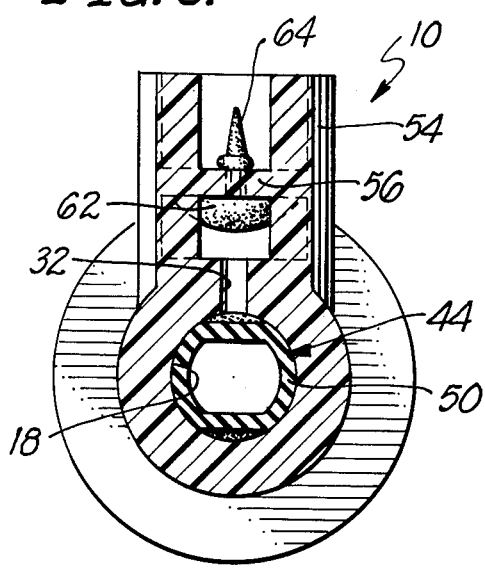
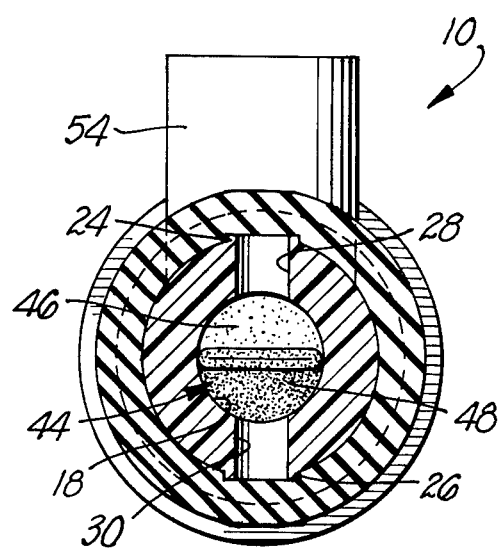

SUCTION CONTROL VALVE FOR LEFT VENTRICLE VENTING

CROSS REFERENCE

This application is a continuation-in-part of U.S. patent application Ser. No. 884,190, filed July 10, 1986 now, U.S. Pat. No. 4,725,266 which is a continuation-in-part of U.S. patent application Ser. No. 715,928, filed March 25, 1985 for "LEFT VENTRICLE VACUUM CONTROL AND PRESSURE RELIEF VALVE," now U.S. Pat. 4,642,097.

BACKGROUND OF THE INVENTION

This invention is directed to a valve which limits the vacuum applied to the left ventricle during open-heart operation, prevents reverse flow to the heart, and vents the downstream line of gas or blood should pressure rise above atmosphere.

During some open-heart procedures, even though the heart is bypassed with the open-heart tubing, some blood finds its way into the left ventricle of the heart. Unless the blood is drained from the left ventricle, the blood causes the heart to distend. Such distension makes it difficult or impossible to resuscitate the heart at the end of the procedure. For this reason, some surgeons attach a slender tubing to the left ventricle to drain the blood from it. A suction pump may be used to provide the vacuum to remove the blood. Several problems may be caused by such a method. One problem arises if the opening of the drain line tube attaches itself to the inside of the heart chamber. This causes suction to be stopped, and the tubing must be wrenched away from the tissue. This causes trauma to the chamber tissue. The present valve limits the suction intensity to a reasonable level so that it is easier to pull the tube away from tissue.

Another problem which may occur during left heart venting arises from the fact that the amount of suction through the left ventricle drain line to the heart is regulated by the speed of the vacuum pump. The vacuum pump is controlled by the heart-lung machine technician who is not close to the surgical field, so the amount of suction intensity must be limited to prevent collapse of the tubing or tissue trauma when the distal end of the line is occluded.

Another problem which may occur is the buildup of pressure in the left ventricle drain line. This would drive air into the heart and cause an air embolism and even possible death of the patient. Such inadvertent pressure in the left ventricle drain line could be caused by any one of several means. For example, the vacuum pump switch could accidentally be positioned to run the pump in reverse so that, instead of suction, pressure would be produced in the drain line. Another possible cause of such pressure would occur when the suction pump is connected to discharge into a closed reservoir in which the pump causes a pressure buildup. In such a case, there is a chance that when the pump is stopped, the pressure may leak back through the drain line into the heart. Another cause of pressure buildup in the drain line is in the structure of the roller pump. In a roller pump, the tubing may be accidentally inserted in a backward orientation into the pump housing so that, even if the pump switch is in the "Forward" position, the pump is working backward.

In order to prevent such problems from causing dangers to the patient, the present left ventricle vacuum control and pressure relief valve was created. This valve prevents flow toward the heart and allows flow only away from the heart, whether the flow be blood or air. A vacuum vent in the valve body is covered on the interior by a resilient umbrella so that the vacuum drawn downstream and upstream of the check valve is limited. Furthermore, the valve of this invention permits any above atmospheric pressure in the downstream line to be vented to the atmosphere instead of being transmitted to the heart. When the venting is accompanied by the escape of blood from the valve, the surgeon is immediately notified that something is wrong (for example, there is inadequate suction to remove the blood) and can take corrective measures.

SUMMARY OF THE INVENTION

In order to aid in the understanding of this invention, it can be stated in essentially summary form that it is directed to a suction control valve for left ventricle venting which includes a body having a passage therethrough and a check valve therein which permits flow only from the inlet toward the outlet. Downstream of the check valve is a pressure vent valve and an umbrella vacuum vent valve which allows air to bleed into the passage when vacuum is applied.

It is, thus, an object and advantage of this invention to provide a valve for the left ventricle drain line which permits flow only away from the heart.

It is another purpose and advantage of this invention to provide a valve for the left ventricle drain line which does not allow full vacuum to be applied to the heart.

It is a further object and advantage of this invention to provide a valve for the left ventricle drain line which automatically vents pressure in excess of atmospheric pressure to prevent pressure buildup toward the heart, and to vent air if pressure builds up in the outlet end of the drain line.

It is a further object and advantage of this invention to provide a valve for the left ventricle drain line which is simple, small, and can be accurately mass-produced and pre-sterilized so that it can be easily and safely inserted in the left ventricle drain.

Other objects and advantages of this invention will become apparent from a study of the following portion of this specification, the claims and the attached drawings.

BRIEF DESCRIPTION OF THE DRAWINGS

FIG. 1 is a side-elevational view of the valve in accordance with this invention.

FIG. 2 is an enlarged section taken generally along the line 2—2 of FIG. 1.

FIG. 3 is a further enlarged transverse section taken generally along the line 3—3 of FIG. 2.

FIG. 4 is an enlarged section taken generally along the line 4—4 of FIG. 2.

DESCRIPTION OF THE PREFERRED EMBODIMENT

The left ventricle vacuum limit and pressure relief valve of this invention is generally indicated at 10 in FIGS. 1, 2, 3 and 4. Valve 10 is shown in longitudinal section in FIG. 2 and is shown in transverse section in FIGS. 3 and 4. Valve 10 has a body 12 and an inlet fitting 14. Body 12 has an outlet barbed nipple 16 on its outlet end with the nipple sized to be received in the left ventricle drain line. Passage 18 in the body adjoins passage 20 in the nipple, with the passages extending end-to-end through the body, defining a central axis there through.

Body 12 has an external surface 22 which is cylindrical about the axis, except for nipples 24 and 26 respectively at the outlet ends of pressure relief passages 28 and 30. Shoulder 33 extends radially outward at the right end of the body. Relief passages 28 and 30 are radial passages of circular cross section which extend from the internal passage 18 to the external surface 22. Vacuum vent passage 32 also is a radially oriented passage of circular cross section extending from the internal passage 18 outward through the body.

Cap 14 has a barbed inlet nipple 34 thereon sized the same as nipple 16 so that the left ventricle drain line can be cut at an appropriate location and the valve 10 inserted therein, with the valve connected to both ends of the line. Body 12 has a circular flange 36 extending to the left therefrom, as seen in FIG. 2, which embraces around a rightward extending circular extension 38 of the cap 14. These interengaging portions provide alignment for the cap on the body and provide for securement of the cap on the body, as by adhesive means, heat sealing, or preferably by ultrasonic bonding.

Inlet nipple 34 and cap 14 also have passage 42 therein which is in alignment with passages 18 and 20. Duckbill valve 44 is structured so that it permits flow from left to right through valve 10, as seen in FIG. 2, in the inlet nipple 34 and out of outlet nipple 16. The valve 44 is an elastomeric molding of generally cylindrical configuration, but, as seen in FIG. 4, has a pair of flat lips 46 and 48 which lie together. These are conventionally molded in one piece and slit afterwards. The result is a valve which opens to flow in the left-to-right direction with very low differential pressure and lies closed essentially without a differential pressure. If the pressure is higher on the right side, as seen in FIG. 2, the valve lips are forced closed to inhibit flow. Such valves are often called "duckbill" valves from their physical resemblance. Thus, valve 44 is a check valve which permits flow only in the left-to-right direction through valve 10. Passage 42 aligns with the interior opening within valve 44, while passage 18 embraces the main body 50 of valve 44. An outwardly directed flange 52 is captured between the body 12 and extension 38 on cap 14.

The cylindrical body 50 of duckbill valve 44 preferably does not occlude vacuum passage 32, as seen in FIGS. 2 and 3. However, should it cover the inside of passage 32, the valve 44 pulls away from passage 32 when vacuum exists inside the valve. Tubular boss 54 is secured on the side of body 12 over the vacuum passage 32, as is seen in FIGS. 2 and 3. Flange 56 extends across the open interior of tubular boss 54. Flange 56 has vent openings 58 therethrough arranged in a circular pattern around central opening 60, see FIG. 1. Umbrella valve 62 has its umbrella positioned on the inside of flange 56 and covering the vent openings 58. The stem 64 of the umbrella valve is barbed and extends upward through the central opening 60 to retain the umbrella valve in place. The umbrella valve is made of synthetic elastomeric material and can be molded to be very precise in its opening characteristic. The stress in the umbrella when installed keeps the vent openings 58 closed until the vacuum in outlet passage 20 goes too far below atmospheric pressure (approximately 125 mm Hg). Thereupon, the atmospheric pressure overcomes the resilient stress of the umbrella and the atmospheric pressure causes the umbrella to bend downward to admit atmospheric air. In this way, the lower limit of pressure downstream of the check valve 44 is controlled. It is to be noted that the entry of air in through the umbrella valve is downstream of the check valve so that it is isolated from the left ventricle.

Elastic ring 66 is engaged around external surface 22 and lies against shoulder 33. Elastic ring 66 is a cylindrical tube which gently engages upon surface 22 and on nipples 24 and 26. When the pressure rises in the central chamber of valve 10, in passage 18, the pressure in relief passages 28 and 30 lifts elastic ring 66 to permit venting of the pressure. However, when there is vacuum in passage 18, elastic ring 66 overlies the openings of relief passages 28 and 30 to prevent inflow from atmosphere. Thus, elastic ring 66 serves as a one-way valve and as the active member in the pressure relief function of valve 10.

As an economic and satisfactory method of manufacture, the body 12, cap 14 and sleeve 54 can be injection-molded of fairly rigid thermoplastic synthetic polymer composition biocompatible material such as polycarbonate or ABS. Almost all surfaces of the valve are surfaces of revolution about the axial centerline through the valve. This design reduces molding costs so as to provide an economic valve. Valve 48 is injection-molded of an elastomer, and after the molding, the valve opening is cut with a razor or the like. Elastic ring 66 can be sliced from an extruded tube or can be molded from thermoplastic elastomer. (As illustrated, the elastic ring 66 is of two external diameters and thus must be molded.) The larger diameter over the nipples 24 and 26 is to permit a heavier elastic force of the ring onto the closure of the pressure relief passages. The level of pressure relief can be controlled by the diameter, hardness, and thickness of the ring. After the assembly of the parts into the organization shown in FIG. 2, the structure is permanently assembled by attachment between flange 36 and extension 38. All of the parts must be of suitable characteristics for sterilization.

In the preferred utilization, the valve 10 is placed in the left ventricle vent line about 2 feet from and level with the heart so that the valve is positioned near the patient's groin on the sterile drape so that it may be observed by the surgeon. Alternatively, the valve can be placed in the line closer to the perfusionist's pump. The amount of suction desired in most cases is about 100-125 mm Hg. The pump speed is adjusted so that this level of vacuum is reached. Should the suction pump not be operating or should the suction pump be operating too slowly and the heart is putting blood into the left ventricle drain line, blood in the valve will leak out of the valve through relief passages 28 and 30. This presence of blood will immediately warn the surgical team of an undesirable condition. Efforts can be made to increase suction to withdraw the blood from the left ventricle drain line. In this manner, the blood is safely drained from the left ventricle, with the level of vacuum being limited by umbrella valve 62 to a proper level. The valve 10 incorporates structure which permits the relief of pressure and incorporates structure which prevents the reverse flow of fluid through the left ventricle drain line and, accordingly, the requirements of the application are satisfied.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed:

1. A valve for the control of vacuum in a physiological liquid drain line, said valve comprising:
   a valve body connectible in the drain line between a patient and a suction pump, said body having a flow passage therethrough having an inlet end and an outlet end, a tubular boss on said body, a vacuum vent opening in said body and said boss, said opening extending radially from said passage through said body through said tubular boss to the atmosphere, a perforated flange in said tubular boss, a resilient umbrella valve on the side of said flange toward said passage covering the perforation in said flange to limit the vacuum in said flow passage;
   walls defining a pressure relief passage in said body extending from said flow passage to the exterior of said body, said walls defining a nipple around said pressure relief passage extending outward from said body; and
   a tubular elastomeric member on said body engaged on said nipple and covering said pressure relief passage so that when pressure in said flow passage is below atmospheric pressure said pressure relief passage is closed and when pressure in said flow passage is above atmospheric pressure, fluid in said flow passage discharges out of said pressure relief passage through said nipple out from under said tubular elastomeric member.

2. The valve of claim 1 further including a check valve within said body for allowing flow through said passage through said body from said inlet end of said body to said outlet end of said body.

3. The valve of claim 2 wherein said passage through said tubular boss is positioned between said check valve and said outlet end of said body.

4. The valve of claim 3 wherein said check valve is a duckbill valve.

5. A valve comprising:
   a valve body, an inlet connection and an outlet connection on said valve body for connection in a drain line between a patient and a suction pump, a passage through said valve body from said inlet to said outlet, walls on said body defining a substantially cylindrical exterior surface;
   a vacuum vent passage in said body from said through passage to the exterior of said body;
   an elastomeric umbrella valve within said valve body lying against the interior of said vacuum vent passage in said body so that when the pressure within said passage falls below a predetermined valve air flows in through said vacuum vent passage to limit the degree of vacuum within said passage;
   walls defining a relief passage in said valve body extending from said through passage to the exterior of said body and defining a nipple extending outward beyond said exterior surface with said relief passage extending through said nipple; and
   an elastomeric member on said body over said nipple and covering said relief passage so that when pressure in said through passage is below external pressure said relief passage is closed and when pressure in said through passage is above external pressure, fluid in said through passage discharges out of said relief passage out from under said elastomeric member.

6. The valve of claim 5 further including a check valve within said body for limiting flow through said passage through said body from said inlet end of said body to said outlet end of said body.

7. The valve of claim 6 wherein said vaccum vent passage through said valve is positioned between said check valve and said oulet from said body.

8. The valve of claim 6 wherein said check valve is a duckbill valve.

9. The valve of claim 6 wherein said check valve is a duckbill valve.

10. A valve comprising:
    a valve body, an inlet connection and an outlet connection on said valve body for connection in a drain line between a patient and a suction pump, a passage through said valve body from said inlet connection to said outlet connection, said valve body having a substantially cylindrical external surface thereon and having a nipple extending therefrom;
    a tubular boss on said body, a flange across said boss, a vacuum vent passage in said flange from said passage to the external surface of said flange;
    a resilient umbrella valve positioned within said flange and lying against the interior surface of said flange and covering said vacuum vent passage where it passes through said flange, said resilient umbrella valve being of such resilience and said vacuum vent passage being of such size as to permit venting of atmospheric air inward into said valve body through said vacuum vent passage;
    a relief passage in said body from said passage to the exterior of said body through the substantially cylindrical external surface of said body and through said nipple;
    an elastomeric member on the exterior of said body, said elastomeric member overlying said nipple and said relief passage in said body so that said elastomeric member acts to vent pressure from the passage through said body to the exterior of said body; and
    a check valve within said body to limit flow through said passage through said body from said inlet to said outlet.

11. The valve of claim 10 wherein said vacuum vent passage is positioned between said check valve and said outlet.

12. The valve of claim 10 wherein said boss is a cylindrically tubular boss and said flange lies thereacross so that said umbrella valve lies within said tubular boss.

* * * * *